United States Patent
Caro et al.

(10) Patent No.: US 7,951,273 B2
(45) Date of Patent: *May 31, 2011

(54) ELECTROCHEMICAL GAS GENERATOR FOR CARBON MONOXIDE

(75) Inventors: Kerstin Caro, Timmendorfer Strand (DE); Peter Tschuncky, Luebeck (DE); Herbert Kiesele, Luebeck (DE)

(73) Assignee: Draeger Safety AG & Co. KGaA, Luebeck (DE)

(*) Notice: Subject to any disclaimer, the term of this patent is extended or adjusted under 35 U.S.C. 154(b) by 905 days.

This patent is subject to a terminal disclaimer.

(21) Appl. No.: 11/835,603

(22) Filed: Aug. 8, 2007

(65) Prior Publication Data

US 2008/0041730 A1    Feb. 21, 2008

(30) Foreign Application Priority Data

Aug. 16, 2006  (DE) .................... 10 2006 038 364

(51) Int. Cl.
*C25B 1/00* (2006.01)
(52) U.S. Cl. ..................... 204/230.2; 204/266
(58) Field of Classification Search .................. None
See application file for complete search history.

(56) References Cited

U.S. PATENT DOCUMENTS

| | | | |
|---|---|---|---|
| 5,061,631 A | 10/1991 | Calabrese | |
| 5,968,325 A * | 10/1999 | Oloman et al. | 204/230.5 |
| 6,200,443 B1 | 3/2001 | Shen et al. | |
| 6,387,228 B1 * | 5/2002 | Maget | 204/230.2 |
| 6,780,304 B1 * | 8/2004 | Maget | 205/555 |
| 7,316,857 B1 * | 1/2008 | Swanson et al. | 429/421 |
| 2003/0145644 A1 | 8/2003 | Rabbett et al. | |
| 2006/0118416 A1 | 6/2006 | Liu et al. | |
| 2006/0283707 A1 * | 12/2006 | Kuhn | 204/424 |

FOREIGN PATENT DOCUMENTS

| | | |
|---|---|---|
| DE | 44 25 889 A1 | 3/1996 |
| EP | 0 611 112 A1 | 8/1994 |
| EP | 0 744 620 A1 | 11/1996 |
| EP | 0 890 837 A2 | 1/1999 |
| EP | 1 530 042 A1 | 5/2005 |
| GB | 2291189 A | 1/1996 |
| GB | WO 99/24826 | 5/1999 |

(Continued)

OTHER PUBLICATIONS

Albalat et al, Electrocatalytic oxidation of mesoxalic acid on a polycrystalline platinum electrode in acid medium, 1989, Electrochimica Acta, vol. 34, No. 5, pp. 611-618.*

(Continued)

*Primary Examiner* — Harry D Wilkins, III
(74) *Attorney, Agent, or Firm* — McGlew and Tuttle, P.C.

(57) ABSTRACT

An electrochemical gas generator is provided including an electrolysis cell (1) with a gas-impermeable housing, which is closed by a gas-permeable membrane (2) for the discharge of the test gas or calibrating gas CO. A chemically inert cathode (5) formed of a noble metal, a mixture of noble metals or a material containing carbon, is in direct contact with an electrolyte (7). An anode (4) formed of a noble metal, a mixture of noble metals or a material containing carbon, is in direct contact with a mesoxalic acid salt, the mesoxalic acid salt being in direct contact with the electrolyte (7). A control unit (6) is provided that also acts as a power source and is connected to the electrodes (4, 5).

13 Claims, 1 Drawing Sheet

FOREIGN PATENT DOCUMENTS

| | | |
|---|---|---|
| GB | 2 356 708 | 5/2001 |
| GB | 2407870 A | 5/2005 |
| WO | WO 01/98767 A2 | 12/2001 |

OTHER PUBLICATIONS

R. Doelling, Potentiostats, Mar. 2000, retrieved from http://www.bank-ic.de/encms/downloads/potstae2.pdf.*

Gore Excellerator Gas Diffusion Membranes Product Data Sheet, 2003.*

Le Naour C et al., "Electro-oxidation of dihydroxymalonic acid on polycrystalline platinum electrode", Electrochimica Acta, vol. 44, 1999, pp. 3505-3512, XP004168625.

Prokopowicz et al., "Quartz rod coated with modified silica gel as a source of CO and $CO_2$ for standard gaseous mixtures", HRC Journal of High Resolution Chromatography, May 1998, vol. 21, No. 5, pp. 303-307, Accession No. PREV199800342262.

* cited by examiner

ELECTROCHEMICAL GAS GENERATOR FOR CARBON MONOXIDE

CROSS REFERENCE TO RELATED APPLICATIONS

This application claims the benefit of priority under 35 U.S.C. §119 of German Patent Application DE 10 2006 038 364.8 filed Aug. 16, 2006, the entire contents of which are incorporated herein by reference.

FIELD OF THE INVENTION

The present invention pertains to an electrochemical gas generator for carbon monoxide (CO).

BACKGROUND OF THE INVENTION

To test the function of and to calibrate gas sensors, the measured gas to be detected or a substitute gas that appears to be suitable is, in general, admitted to the gas sensors at fixed time intervals. It is either possible to use this test gas in compressed gas containers together with suitable gas admission means, for example, with pressure reducers, or to generate the test gas directly and to apply it to the sensor through suitable gas admission devices. The use of compressed gas containers with corresponding means is complicated and requires corresponding logistics and handling.

No commercially available gas generators which can generate the test gas CO are currently available for testing the function of carbon monoxide sensors. Only the generation of CO with the use of carbon electrodes by means of electrolytic oxygen generation and subsequent reaction of the carbon electrode itself to form a mixture of CO and $CO_2$ is described in US 2003 014 5644, but it found no application in a commercial product. The reason for this might be the drawbacks of the use of such consuming electrodes, because sufficient long-term stability of a generator cannot be attained with such a design and the reaction is strongly affected by the climatic conditions prevailing at the time of the testing, such as temperature and relative humidity, as a result of which greatly fluctuating CO contents will be obtained in the test gas.

Substitute gas calibration with hydrogen ($H_2$) is therefore frequently used as an alternative, as is described, for example, in WO/99 24 826, but this does not make it possible to directly infer the sensitivity of the gas sensor to be tested to the primary test gas, because the reaction of $H_2$ may very well be successful on a poisoned catalytic material of a corresponding electrochemical gas sensor that is consequently no longer suitable for measurement, whereas the same catalytic material does not react CO electrochemically any longer, i.e., the calibration is incorrect.

SUMMARY OF THE INVENTION

Consequently, there is a need for providing an electrochemical gas generator with the highest long-term stability possible for carbon monoxide.

According to the invention, an electrochemical gas generator is provided comprising an electrolysis cell with a gas-impermeable housing, which is closed by a gas-permeable membrane for the discharge of the test gas or calibrating gas CO. A cathode is formed of a noble metal, a mixture of noble metals or a material containing carbon. This cathode is in direct contact with an electrolyte. An anode is formed of a noble metal, a mixture of noble metals or a material containing carbon. This anode is in direct contact with the electrolyte containing a mesoxalic acid or a mesoxalate. A control unit acts as a power source and is connected to the electrodes.

A reference electrode may advantageously be provided in contact with the electrolyte in the electrolysis cell. The control unit may also comprise a potentiostat.

The cathode and the anode may advantageously consist of platinum and the anode may be embodied as a mesh.

The substance reacted at the anode may be a mesoxalate, preferably an alkali metal salt, an alkaline earth metal salt or an ammonium salt of mesoxalic acid, preferably sodium mesoxalate.

The substance reacted at the anode may contain a mesoxalic acid or a mesoxalate. This is used preferably in the form of a molding placed on the anode or in the form of a structure compressed around the anode.

The electrolyte used, in which the mesoxalic acid or mesoxalate is used, may advantageously be poorly soluble.

An organic electrolyte may be used, which preferably consists of a mixture of propylene and ethylene carbonates.

The test gas or calibrating gas CO may be formed by decarboxylation from a mesoxalic acid or a mesoxalate at the anode.

The molding may be disposed directly adjacent to the membrane with a contacting platinum mesh connected as an anode.

The housing of the electrolysis cell may advantageously be formed of one or more of polyethylene and polypropylene.

The membrane may be formed of a microporous perfluorinated polymer.

Contrary to previous studies by other working groups, such as C. Le Naour, Ph. Moisy, S. Arpigny and C. Madic, *Electrochimica Acta*, Vol. 44, No. 20, pp. 3505-3512, it was surprisingly found that carbon monoxide can be produced by a suitable electrolysis of mesoxalic acid salts and especially sodium mesoxalate by double decarboxylation at the anode. The $CO_2$ formed simultaneously is not disturbing in case of the electrochemical CO gas sensors tested or to be tested because there is no cross sensitivity in this respect.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
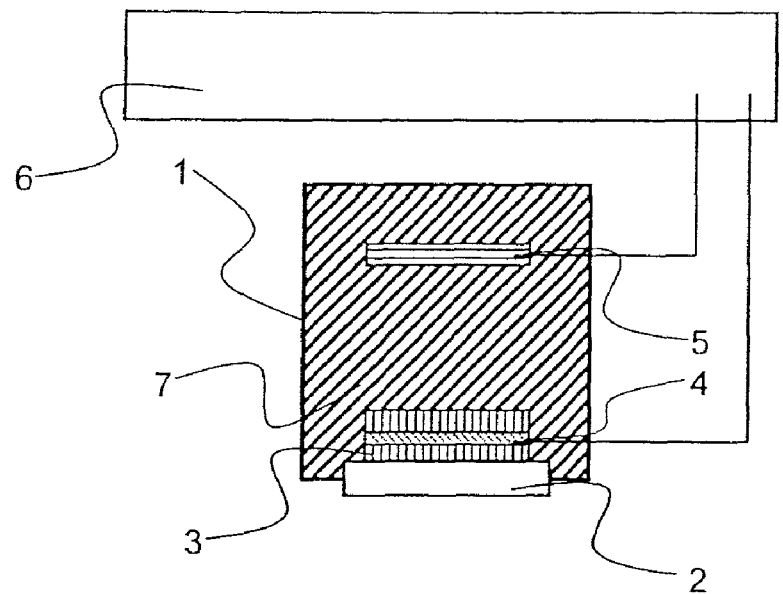
FIG. 1 is a schematic view of an electrochemical gas generator according to the invention for generating a test gas or calibrating gas CO showing the most important components.
Figure 2:
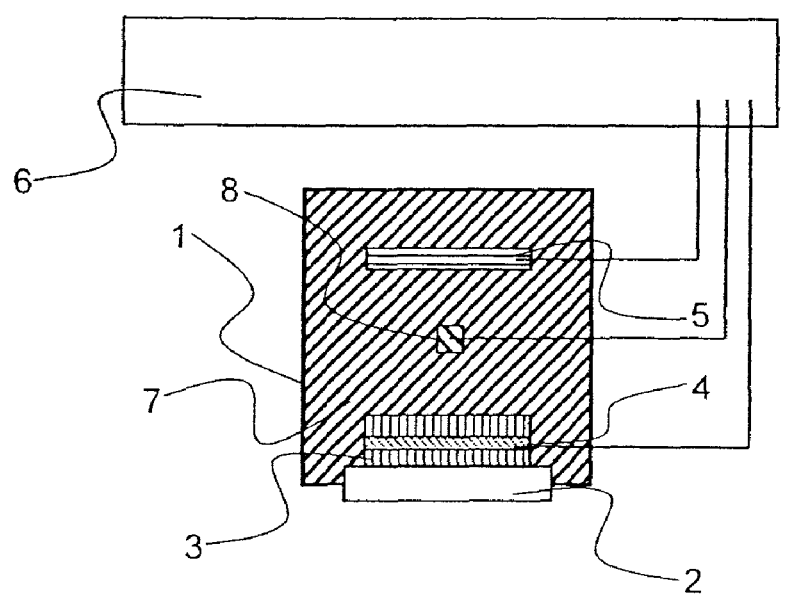
FIG. 2 is a schematic view of another electrochemical gas generator according to the invention for generating a test gas or calibrating gas CO showing the most important components.

Referring to the drawings in particular of FIGS. 1 and 2 show exemplary embodiments of the present invention of an electrochemical gas generator for the test gas or calibrating gas CO with the most important components.

A molding 3 of the mesoxalic acid salt sodium mesoxalate is reacted electrochemically by means of a platinum mesh connected as an anode 4 in an electrolysis cell, which is closed by a membrane 2 that is permeable to gas.

An electrode made of platinum is likewise used preferably as the cathode 5. The electrodes 4, 5 are connected to a control unit 6, which also acts as a power source. If an electrolysis is now carried out in an electrolyte 7, especially one consisting of a mixture of propylene and ethylene carbonates (weight ratio approximately 6:4) by means of a connected power source, the following two reactions will take place at the anode 4:

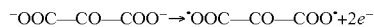

The $CO/CO_2$ mixture formed at the anode 4 leaves the housing of the electrolysis cell 1 through the permeable membrane 2 at a concentration ratio of 1:2 and can be used as a test or calibrating gas for a gas sensor, which is in connection with the test gas or calibrating gas.

FIG. 2 shows another embodiment of the gas generator for CO according to the present invention. A reference electrode 8 is additionally introduced here into the electrolysis cell in direct contact with the electrolyte 7.

Both a power source and a unit containing a potentiostat may be used as the control unit 6 for both embodiments described.

While specific embodiments of the invention have been shown and described in detail to illustrate the application of the principles of the invention, it will be understood that the invention may be embodied otherwise without departing from such principles.

What is claimed is:

1. An electrochemical gas generator comprising:
an electrolysis cell with a gas-impermeable housing, which is closed by a gas-permeable membrane for the discharge of a test gas CO or a calibrating gas CO;
an electrolyte containing a mesoxalic acid or a mesoxalate;
a cathode formed of a noble metal, a mixture of noble metals or a material containing carbon, said cathode being in direct contact with said electrolyte;
an anode formed of a noble metal, a mixture of noble metals or a material containing carbon, said anode being in direct contact with said electrolyte;
a control unit acting as a power source, said control unit being connected to said anode and said cathode and controlling electrolysis to react mesoxalic acid or a mesoxalate at the anode to form said test gas CO or said calibrating gas CO by decarboxylation from the mesoxalic acid or the mesoxalate reacted at said anode; and
a reference electrode in contact with said electrolyte in said electrolysis cell, wherein a substance reacted at said anode contains a mesoxalic acid or a mesoxalate and is provided as a molding wherein said molding is directly adjacent to said membrane with said anode provided as a contacting platinum mesh.

2. An electrochemical gas generator in accordance with claim 1, wherein said control unit further comprises a potentiostat.

3. An electrochemical gas generator in accordance with claim 1, wherein said cathode consists of platinum.

4. An electrochemical gas generator in accordance with claim 1, wherein said mesoxalate is at least one of an alkali metal salt, an alkaline earth metal salt, an ammonium salt of mesoxalic acid and sodium mesoxalate.

5. An electrochemical gas generator in accordance with claim 1, wherein said housing is formed of one or more of polyethylene and polypropylene.

6. An electrochemical gas generator in accordance with claim 1, wherein said membrane consists of a microporous perfluorinated polymer.

7. An electrochemical gas generator comprising:
an electrolysis cell with a gas-impermeable housing, which is closed by a gas-permeable membrane for the discharge of a test gas or a calibrating gas CO;
an electrolyte containing a mesoxalic acid or a mesoxalate;
a cathode formed of a noble metal, a mixture of noble metals or a material containing carbon, said cathode being in direct contact with said electrolyte;
an anode formed of a noble metal, a mixture of noble metals or a material containing carbon, said anode being in direct contact with said electrolyte; and
a control unit acting as a power source, said control unit being connected to said anode and said cathode, wherein a substance reacted at said anode contains a mesoxalic acid or a mesoxalate and is provided as a molding placed on said anode or in the form of a structure compressed around said anode.

8. An electrochemical gas generator comprising:
an electrolysis cell with a gas-impermeable housing, which is closed by a gas-permeable membrane for the discharge of a test gas or a calibrating gas CO;
an electrolyte containing a mesoxalic acid or a mesoxalate;
a cathode formed of a noble metal, a mixture of noble metals or a material containing carbon, said cathode being in direct contact with said electrolyte;
an anode formed of a noble metal, a mixture of noble metals or a material containing carbon, said anode being in direct contact with said electrolyte; and
a control unit acting as a power source, said control unit being connected to said anode and said cathode, wherein said electrolyte is selected such that mesoxalic acid or mesoxalate is poorly soluble in said electrolyte.

9. An electrochemical gas generator comprising:
an electrolysis cell with a gas-impermeable housing, which is closed by a gas-permeable membrane for the discharge of a test gas or a calibrating gas CO;
an electrolyte containing a mesoxalic acid or a mesoxalate;
a cathode formed of a noble metal, a mixture of noble metals or a material containing carbon, said cathode being in direct contact with said electrolyte;
an anode formed of a noble metal, a mixture of noble metals or a material containing carbon, said anode being in direct contact with said electrolyte; and
a control unit acting as a power source, said control unit being connected to said anode and said cathode, wherein said electrolyte is an organic electrolyte including a mixture of propylene and ethylene carbonates.

10. An electrochemical gas generator comprising:
an electrolysis cell with a gas-impermeable housing, which is closed by a gas-permeable membrane for the discharge of a test gas or a calibrating gas CO;
an electrolyte;
a cathode formed of at least one of a noble metal, a mixture of noble metals and a material containing carbon, said cathode being in direct contact with said electrolyte;
an anode formed of at least one of a noble metal, a mixture of noble metals and a material containing carbon, said anode being in direct contact with said electrolyte;
a mesoxalic acid or a mesoxalate provided in said electrolyte as a substance reacted at said anode; and
a control unit acting as a power source, said control unit including a potentiostat and being connected to said cathode and said anode, wherein the substance reacted at said anode which contains a mesoxalic acid or a mesoxalate is provided as a molding wherein said molding is directly adjacent to said membrane with said anode provided as a contacting platinum mesh.

11. An electrochemical gas generator in accordance with claim 10, further comprising a reference electrode in contact with said electrolyte in said electrolysis cell.

12. An electrochemical gas generator in accordance with claim 10, wherein said mesoxalate is at least one of an alkali metal salt, an alkaline earth metal salt, an ammonium salt of mesoxalic acid and sodium mesoxalate.

13. An electrochemical gas generator in accordance with claim 10, wherein said housing is formed of one or more of polyethylene and polypropylene and said membrane consists of a microporous perfluorinated polymer.

* * * * *